United States Patent
Yaqub et al.

(10) Patent No.: US 10,762,630 B2
(45) Date of Patent: Sep. 1, 2020

(54) SYSTEM AND METHOD FOR STRUCTURES DETECTION AND MULTI-CLASS IMAGE CATEGORIZATION IN MEDICAL IMAGING

(71) Applicant: Oxford University Innovation Limited, Oxford (GB)

(72) Inventors: Mohammad Yaqub, Oxford (GB); J. Alison Noble, Oxford (GB); Aris Papageorghiou, Oxford (GB)

(73) Assignee: OXFORD UNIVERSITY INNOVATION LIMITED (GB)

( * ) Notice: Subject to any disclaimer, the term of this patent is extended or adjusted under 35 U.S.C. 154(b) by 221 days.

(21) Appl. No.: 15/744,371

(22) PCT Filed: Jul. 15, 2016

(86) PCT No.: PCT/IB2016/054251
§ 371 (c)(1),
(2) Date: Jan. 12, 2018

(87) PCT Pub. No.: WO2017/009812
PCT Pub. Date: Jan. 19, 2017

(65) Prior Publication Data
US 2019/0385307 A1    Dec. 19, 2019

Related U.S. Application Data

(60) Provisional application No. 62/192,905, filed on Jul. 15, 2015.

(51) Int. Cl.
*G06T 7/00* (2017.01)
*G06K 9/46* (2006.01)
(Continued)

(52) U.S. Cl.
CPC .......... *G06T 7/0014* (2013.01); *G06K 9/4647* (2013.01); *G06K 9/628* (2013.01);
(Continued)

(58) Field of Classification Search
CPC ... G06T 7/0012; G06T 7/0014; G06K 9/6202; G06K 9/6203; G06K 9/6857; G06K 2209/05; A61B 8/5223
See application file for complete search history.

(56) References Cited

U.S. PATENT DOCUMENTS

| | | | | |
|---|---|---|---|---|
| 6,640,008 B1 * | 10/2003 | Lee et al. | ............ | G06K 9/4647 382/170 |
| 2006/0110035 A1 | 5/2006 | Luo et al. | ...................... | 382/170 |
| 2017/0072222 A1* | 3/2017 | Siversson | ............ | A61N 5/1039 |

FOREIGN PATENT DOCUMENTS

| | | | | |
|---|---|---|---|---|
| WO | 02/45587 A1 | 6/2002 | ............... | A61B 8/08 |
| WO | 2006/058176 A1 | 6/2006 | ............... | G06T 7/00 |

OTHER PUBLICATIONS

International Search Report and Written Opinion for International Application PCT/IB2016/054251 dated Nov. 3, 2016, 18 pages.
(Continued)

*Primary Examiner* — Andrew W Johns
(74) *Attorney, Agent, or Firm* — Thomas|Horstemeyer, LLP

(57) ABSTRACT

A system and method are provided to automatically categorize biological and medical images. The new system and method can incorporate a machine learning classifier in which novel ideas are provided to guide the classifier to focus on regions of interest (ROI) within medical images for categorizing or classifying the images. The system and method can ignore regions when misleading structures exist. The detection and classification of one or more features of interest within a discriminative region of interest within an image are rendered invariant to differences in translation, orientation and/or scaling of the one or more features of interest within the medical image(s). The system and method allow a processor to more quickly, efficiently and accurately process and categorize medical images.

15 Claims, 9 Drawing Sheets

(51) Int. Cl.
*G06K 9/62* (2006.01)
*G06K 9/68* (2006.01)

(52) U.S. Cl.
CPC ......... *G06K 9/6228* (2013.01); *G06K 9/6857* (2013.01); *G06K 2209/05* (2013.01); *G06T 2207/10132* (2013.01); *G06T 2207/20021* (2013.01); *G06T 2207/20081* (2013.01); *G06T 2207/30044* (2013.01)

(56) References Cited

OTHER PUBLICATIONS

Yang Xin et al., "Standard plane localization in ultrasound by radial component", 2014 IEEE 11th International Symposium on Biomedical Imaging (ISBI), Apr. 29, 2014, pp. 1180-1183.

* cited by examiner

... etc

SYSTEM AND METHOD FOR STRUCTURES DETECTION AND MULTI-CLASS IMAGE CATEGORIZATION IN MEDICAL IMAGING

CROSS-REFERENCE TO RELATED DOCUMENTS

This application is the National Stage of International Application No. PCT/IB2016/054251, filed 15 Jul. 2016, having the title "SYSTEM AND METHOD FOR STRUCTURES DETECTION AND MULTI-CLASS IMAGE CATEGORIZATION IN MEDICAL IMAGING", which claims the benefit of and priority to U.S. Application No. 62/192,905, filed on 15 Jul. 2015, the contents of all of which are incorporated by reference as if fully set forth herein.

This application makes reference to and incorporates by reference the following paper as if it were fully set forth herein expressly in its entirety: Guided Random Forests (RF) for Identification of Key Fetal Anatomy and Image Categorization in Ultrasound Scans, attached hereto as Appendix A.

TECHNICAL FIELD

The present disclosure generally relates to biological and medical imaging, and in particular to categorization of the images acquired over time.

BACKGROUND

Image categorization is a well-known open-research problem in computer vision for which many solutions have been proposed [1-3]. In medical image applications, image categorization is relatively under-investigated but nevertheless important. The volume of digital images acquired in the healthcare sector for screening, diagnosis or therapy is very large and increasing steadily.

For example, ultrasound based fetal anomaly screening is usually performed at 18 to 22 weeks of gestation. Several images of fetal structures are acquired following a standardized protocol. This screening scan aims to determine whether the fetus is developing normally by assessing several ultrasound images of different fetal structures. The number of different structures that are imaged and acquired in a complete scan varies. The UK NHS Fetal Anomaly Screening Programme (FASP) recommends 21 views to be assessed and at least 9 images to be stored. The number of individual women undergoing a scan is often of the order of several thousands per department per annum. Most clinical departments save these scans to an archive system without any labeling of the objects present in an image. This means it is not possible to conveniently recall images of, say, body parts for later review or measurement. Nor is it possible to compare scans of the same fetus over time, or conduct automatic on-line measurement post-acquisition.

Although there are a number of methods which have been proposed to address different medical image categorization problems [4-6], very little research has been done in fetal ultrasound image categorization [4, 7, 8]. This may in part be explained because fetal ultrasound image categorization has unique challenges. The quality and appearance of the images vary for a number of reasons including variation of fetal position, sonographer experience, and maternal factors, all affecting the appearance of images. In addition, a fetal ultrasound image can contain one or more fetal and non-fetal structures. The non-fetal structures can serve as distractions to categorization of the images.

Further, existing medical image classification systems have difficultly discriminating between features of interest and misleading structures or features that can exist in a medical image. The features of interest can be anatomical features in the image. General classification methods apply to a whole image to output a single class or classification and fail to achieve this test robustly. They fail to ignore regions where misleading structures can exist. Moreover, existing classification methods tend to be based on one more prior medical images in which a feature of interest, for example an anatomical feature of interest, has been identified and tagged as representative of the feature and used as a basis for correlation to other medical images for classification. Such approaches however have difficulty distinguishing different structures in diverse scenes and structures varying in translation or intention and/or scaling from one image to another image.

Thus, there is a need for a system and method to automatically categorize biological and medial images acquired over time. There is also a need for a system to more quickly, efficiently and accurately process and categorize medical images. In particular there is a need for a system and method to categorize biological and medical images that is discriminative, for example that can be guided to look for features in representative regions of an image while ignoring regions where misleading structures or features exist and that is invariant to translation, orientation and/or scaling of features of interest that can allow distinguishing different structures in diverse scenes.

SUMMARY

Provided herein are a system and method to automatically categorize biological and medical images. The new system and method can incorporate a machine learning classifier in which novel ideas are provided to guide the classifier to focus on regions of interest (ROI) within medical images for categorizing or classifying the images. The system and method can ignore regions when misleading structures exist. The system and method can involve a processor that can more quickly, efficiently and accurately process and categorize medical images As a non-limiting example, our system and method can categorize fetal ultrasound images from anomaly scans.

We reference from time to time herein categorization of fetal ultrasound images because of the unique challenges they pose. Our system and method, however, are not limited to categorization of only fetal ultrasound images or even more generally ultrasound images. They may be applied to categorize any set of biological and/or medical images.

Machine learning methods can learn features from images ignoring the fact that images might contain misleading regions. Therefore, in various aspects the present system and method incorporates a machine learning method that can extract features from important or candidate regions of interest (ROI's) within the images where structures of interest exist. As a result, the robustness and accuracy of the learner will be better. Also as a result, a processor used to categorize and classify medical images can run more quickly, efficiently and accurately.

In various aspects, the present system and method can utilise a machine learning technique (such as Random Forests) which is guided to look for features in representative regions within the images to be categorized. This can help ignore regions where misleading structures exist.

In one or more aspects, representative regions can be detected using template matching. A family of geometric templates can be developed and used to look for and detect one or more features of a structure of interest within the images to be classified to thereby locate and identify one or more structures of interest within the images. By a "family" of templates we mean a set or grouping of templates having varying size (scale) and orientation, each template of the set or grouping including one or more geometric features representative of a structure of interest. The family of templates can also include templates varying in translation and/or variance. As a non-limiting example, each template of the family can include one or more geometric features representative of a stomach, a spine, a rib or rib cage, or a head of a fetus. Thus, in one or more aspects, template matching can be conducted at several scales and orientations. The system and method can integrate translation, orientation and scaling invariant features in the templates which can allow different structures in diverse scenes in the medical image(s) to be correlated to the template features and distinguished in the image(s). The detection of one or more features of interest within a discriminative region of interest can thereby be rendered invariant to differences in translation, orientation and/or scaling of the one or more features of interest within the medical image(s).

Therefore, in an embodiment, we provide a method for categorizing biological and/or medical images. The method can extract features from certain regions of interest (ROI's) within the images while ignoring regions within the images where misleading structures exist. By doing so we can restrict classification to candidate ROI's. Thus, the method can discriminate features within the images extracting those of interest while ignoring those where misleading structures may exist. The method can use a machine learning classifier to carry out the method. The classifier can learn one or more classes of features. The feature detection and classification will not be confused or defeated because of variations in translation, orientation or sealing of the features between images.

The classifier can utilize one or more feature sets. In an aspect, it can utilize two feature sets. One feature set can be a family of templates based on known biology or anatomy (ex., clinical knowledge) or known shapes of manufactured parts (such as may be part of a cluttered scene that may include one or more manufactured parts in the biological or medical image) used to determine the probability that the extracted data contains a structure (e.g., a biological or an anatomical feature, or a manufactured part) of interest (that can be any one or more views). The classifier can learn a model by selecting a set of representative template and image based features. In one or more aspects, a normalized cross-correlation between the image (I) and the template (T), for example between one or more of the representative template based features and image features, can be used to determine the correlation by finding the best match between the template based features and the image features. In one or more aspects, the correlation can be carried out in the spatial Fourier domain as opposed to conventional spatial domain. Another feature set can be extracted from the images which captures the appearance or intensity of regions within the images.

In an embodiment, a technique or method is provided for categorizing biological or medical images which includes: a) obtaining a plurality of biological or medical images depicting one or more structures; b) providing and using a family of multi-resolution, multi-orientation geometric templates that is made translation, orientation and/or scaling invariant by computing correlation with the templates at selected pixels within the images (such as each pixel, or every nth pixel); c) detecting the one or more structures within the images based on the computed correlation; and d) categorizing the biological or medical images by the one or more structures detected. The geometric templates can be for manufactured parts, biological or medical (anatomy) applications.

In any one or more aspects of any one or more of the embodiments herein, the family of geometric templates can be based on clinical knowledge of known biology or anatomy. The step of detecting a region can include discriminating between the image of the one or more structures and misleading structures in the biological or medical images. The step of computing correlation can be carried out using a data parameter selected from the group consisting of the template correlation value (response), the relative size of the region with respect to the original image size, the Euclidean distance measured between the center of the region $C=\{cx, cy\}$ and the center of the image, the location of the top left corner of the region within the image, the location of the bottom right corner of the region, and combinations thereof.

In an embodiment, a method is provided for creating a feature matrix for categorizing biological and/or medical images. The method can include: a) obtaining a biological or medical image depicting one or more structures; b) partitioning the image into blocks; c) computing intensity statistics (e.g., mean, median, maximum, standard deviation, etc.) between the blocks in the region to form a feature matrix (A); d) computing a scalar feature value from the feature matrix (A) such as using a determinant or its rescaled value (e.g., using $\log_e$) to produce a dynamic range; e) creating multiple features for a specific template by varying the block sizes to capture the appearance of the region at different scales depending on the size of the blocks; and f) using the captured appearance of a region to build a machine learning method to categorize the images.

In an embodiment, a machine learning method is provided including a machine learning algorithm to categorize biological and/or medical images using the features (as in the feature matrix (A)) within a classifier to learn a set of discriminative features of the images from the feature pool. This can include:
  a) Guiding the learning algorithm to only focus on highly discriminative regions within the images (which can be computed as in the above correlation); and
  b) Utilizing a template correlation score to define or weight how strongly a feature is depicted within the images, allowing use of any feature in the feature set or a subset of a full feature set which has a large template correlation score to categorize the images.

In an embodiment, a system for categorizing clinical or biological images is provided, comprising: at least one device for receiving a plurality of biological images depicting one or more structures and a family of multi-resolution, multi-orientation geometric templates that is made translation, orientation and/or scaling invariant by computing correlation with the templates at selected pixels within the images (such as at each pixel, or at every with pixel); at least one computing device; and an application executable in the at least one computing device, the application comprising logic that: a) uses the family of multi-resolution, multi-orientation geometric templates by computing correlation at the selected pixels within the images; b) detects the one or more structures within the images based on the computed correlation; and c) categorizes the biological or medical images by the one or more structures detected.

In an embodiment, a non-statutory computer readable medium is provided employing a program executable in at least one computing device, comprising code that: a) receives a plurality of the biological or medical images depicting one or more structures and a family of multi-resolution, multi-orientation geometric templates that is made translation, orientation and/or scaling invariant; b) uses the family of multi-resolution, multi-orientation geometric templates by computing correlation at the selected pixels within the images; c) detects the one or more structures within the images based on the computed correlation; and d) categorizes the biological or medical images by the one or more structures detected.

In an embodiment, a system is provided for creating a feature matrix for categorizing a biological or medical image, comprising: at least one device for receiving the biological or medical image depicting one or more structures; at least one computing device; and an application executable in the at least one computing device, the application comprising logic that: a) partitions a region of the image into blocks; b) computes intensity statistics (e.g., mean, median, maximum, standard deviation, etc.) between the blocks in the region to form a feature matrix (A); c) computes a scalar feature value from the feature matrix (A) such as using a determinant or its rescaled value (e.g., using log e) to produce a dynamic range; d) creates multiple features for a specific template by varying the block sizes to capture the appearance of the region at different scales depending on the size of the blocks; and e) uses the captured appearance of a region to build a method to categorize the images.

In an embodiment, a non-statutory computer readable medium is provided employing a program executable in at least one computing device, comprising code that: a) receives a biological or medical image depicting one or more structures; b) partitions a region of the image into blocks; c) computes intensity statistics (e.g., mean, median, maximum, standard deviation, etc.) between the blocks in the region to form a feature matrix (A); d) computes a scalar feature value from the feature matrix (A) such as using a determinant or its rescaled value (e.g., using log e) to produce a dynamic range; e) creates multiple features for a specific template by varying the block sizes to capture the appearance of the region at different scales depending on the size of the blocks; and f) uses the captured appearance of a region to build a method to categorize the images.

In an embodiment, a system for including a machine learning method and a learning algorithm is provided to categorize biological and/or medical images using the features of the aforementioned feature matrix (A) within a classifier to learn a set of discriminative features of the images from the feature pool, comprising: at least one device for receiving the biological and/or medical images; at least one computing device; and an application executable in the at least one computing device, the application comprising logic that: a) guides the learning algorithm to only focus on highly discriminative regions within the images (which can be computed as in the aforementioned computing correlation); and b) utilizes a template correlation score to define or weight how strongly a feature is depicted within the images, allowing use of any feature in the feature set or a subset of a full feature set which has a large template correlation score to categorize the images.

In an embodiment, a non-statutory computer readable medium is provided employing a program executable in at least one computing device, comprising code that: a) includes a machine learning method and a learning algorithm to categorize biological and/or medical images using the features of the aforementioned feature matrix (A) within a classifier to learn a set of discriminative features of the images from the feature pool, comprising: b) receives a plurality of biological and/or medical images; c) guides the learning algorithm to only focus on highly discriminative regions within the images (which can be computed as in the aforementioned computing correlation); and d) utilizes a template correlation score to define or weight how strongly a feature is depicted within the images, allowing use of any feature in the feature set or a subset of a full feature set which has a large template correlation score to categorize the images.

In any one or more of the aforementioned embodiments, the machine learning technique can be a Random Forests machine learning technique.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
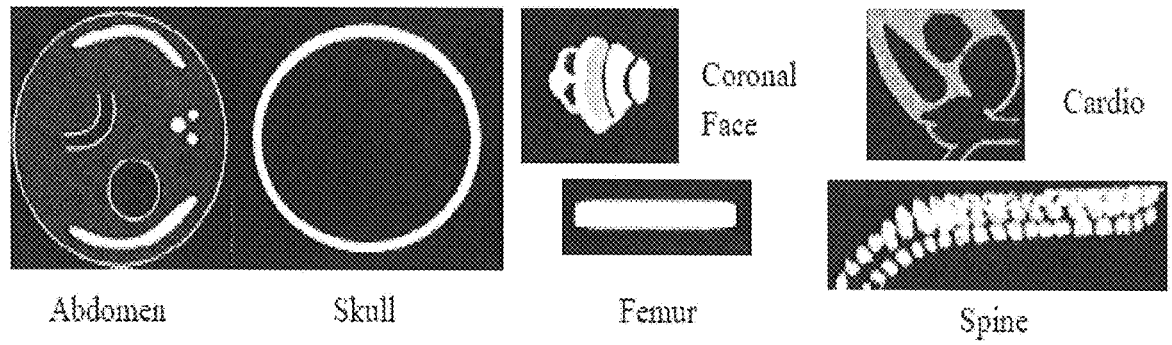
FIG. 1A depicts examples of fetal structure templates that can be used in the present system and method.

Described below are various embodiments of the present systems and methods for structures detection and multi-class image categorization in medical imaging. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

DISCUSSION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers, etc., but some errors and deviations should be accounted for.

It is to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports.

DESCRIPTION

In general, the present system and method can categorize biological and/or medical images based on detection of one or more features within the images. In various aspect, the system and method can discriminate and extract novel features from the medical images (images can be 2D, 3D or of higher dimensions) for categorization of the images. The extracted features can be used to build a classifier which can learn structures within any image. The structures can be related to or directed to particular biology or anatomy within the images or manufactured parts (for example of the type that maybe found in a cluttered scene in a biological or medical image) within the images. The classifier can learn one or more classes which can represent one or more structures within the images. As a non-limiting example, eight classes can be learned which can represent seven anatomical views (and an "unknown" class), such as: 1) head in the trans-ventricular plane (Head TV); 2) head in the trans-cerebellar plane (Head TC); 3) 4-chamber view of the heart (cardio); 4) face (a coronal view of the lips); 5) abdomen (at the level where the abdominal circumference is measured); 6) femur (for the measurement of femur length); 7) spine; and 8) a category called "Others" which may contain many other fetal structures e.g., limbs, kidneys, cord insertion, etc. In the experiments below we show the learning of eight classes or views, however, the actual number of classes or views can be more or less than eight.

The learning can be "guided" because the features can be extracted from regions where structures of interest exist. This can help avoid misleading anatomy within these images. We can further provide a method to build the features computed on these regions in a translation, orientation, and scaling invariant fashion that can make our learning algorithm more robust.

Localizing a Structure of Interest

An objective of the present system and method is to automatically localize one or more structures of interest depicted in the images. In various aspects, they can sample features from within discriminative regions instead of looking blindly across the images. This can be important, for example, in ultrasound imaging where there can be distracting regions of similar appearance. To achieve this a family of geometric templates can be built which can capture one or more structures we are interested in categorizing. In an aspect, multi-resolution and multi-orientation templates can be built to capture the appearance of one or more main structures or features of interest in detecting and categorizing the image(s). In an aspect, the templates can be geometric templates to capture the geometric appearance of the one or more structures. In one or more aspects the template(s), including one or more features of the template(s) can be invariant to translation, orientation and/or scale.

To find a match between an image I and a template T, a correlation can be built between the image I and the template T. In one or more aspects, the correlation can be a cross-correlation, such as a normalized cross correlation. The correlation can be implemented, for example, in the spatial or the Fourier domains.

Parameters for the image region which produce a correlation (preferably, a maximum correlation) with the template can be recorded. In an aspect, 9 parameters can be used. The 9 parameters can be {corr, s, d, $\underline{C}$, $\underline{P_1}$, $\underline{P_2}$} such that corr is the template correlation value (response), s is the relative size of the matched region with respect to the original image size, d is the Euclidean distance measured between the center of the region C={cx, cy} and the center of the image, $\underline{P_1}$={x1, y1} is the location of the top left corner of the matched region within the image, and $\underline{P_2}$={x2, y2} is the location of the bottom right corner. One skilled in the art will recognize that more than 9 parameters or less than 9 parameters can be used.

Figure 1B:
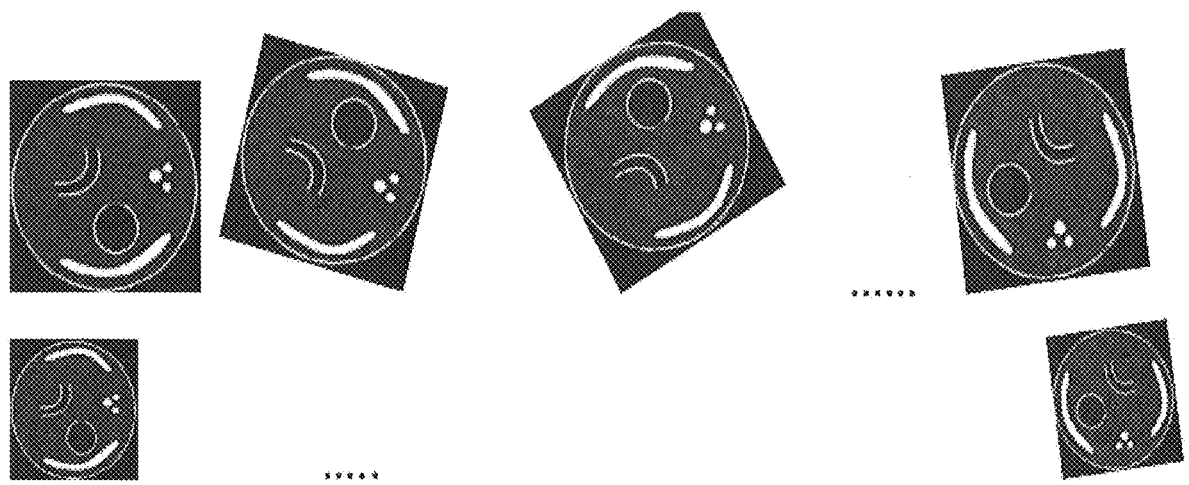
FIG. 1B depicts an example of a family of templates of the abdomen template depicted in FIG. 1A that can be used in the present system and method including templates of varying size (scale), orientation, translation and variance.

As a non-limiting example, established clinical knowledge of fetal anatomy can be used in the family of templates to ensure that their physical size correspond to the size of one or more physiological structures, for example fetal structures. For instance, bi-parietal diameter (the minor axis of the fetal skull) of the fetal skull ranges from 40 mm to 55 mm [10]. FIG. 1A shows an example of different template types that can be used. FIG. 1B shows an example of a family of templates that can be used. This family of templates is based on the abdomen template depicted in FIG. 1A. Other families of templates can be created and used, for example based on the skull, femur, spine templates of FIG. 1A, or other geometric templates. The geometric templates can be for manufactured parts, biological or medical (anatomical) applications. As shown in FIG. 1B, the family of templates includes templates of varying size (scale), orientation (for example rotation), translation and/or variance. The family of templates provides a multi-resolution, multi-orientation set of geometric templates that is made translation invariant by computing correlation (as above) at selected pixels (such as for each pixel, or every nth pixel) within the images.

Figure 2A:
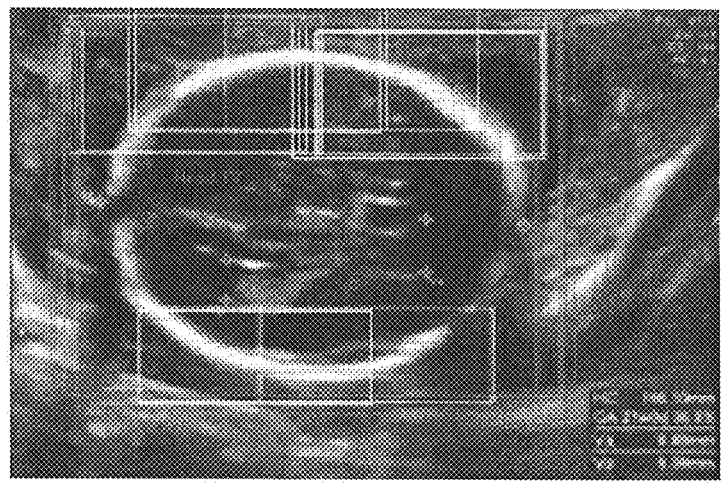
FIGS. 2A-2C depict template responses on three images: (A) Head TV; (B) Abdomen; and (C) Face (regions with high responses are only shown here for convenience). The template response can be depicted as a colored rectangle (see below in the Detailed Description section for color definition).
Figure 2B:
Figure 2C:
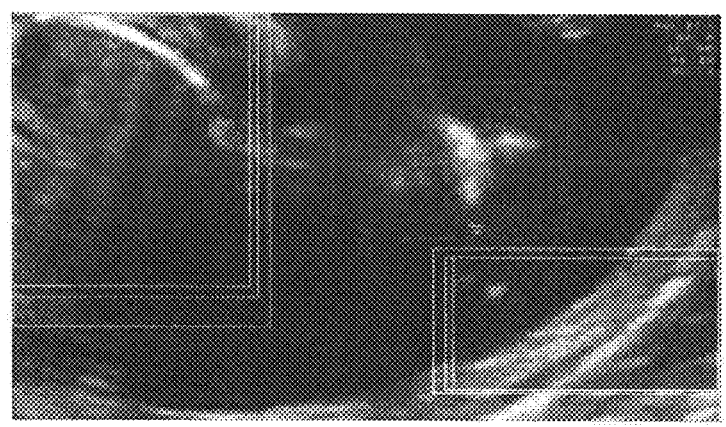

FIG. 2 illustrates matched regions of best-matched templates on three ultrasound images. The particular images are Head TV (FIG. 2A), Abdomen (FIG. 2B) and Face (FIG. 2C). Different colors can be used for different features. For example, green can be used for skull, blue for spine, red for face, magenta for abdomen and yellow for femur, though different color schemes can be used. The width of the border of the box can indicate the strength of the template response (corr).

Feature Set(s) for the Learning Algorithm

In an aspect, the present machine learning solution can utilize a feature set. The feature set can represent template metadata (e.g., corr, s, d, etc.), such as described above. These values can be discriminative since corr provides an indication of how probable it is that a region of interest within an image contains a structure of interest, s indicates how large a region of interest is within an image (e.g., fetal face occupies a small region within an image while a skull is typically larger), and d is the Euclidian distance between the region and the center of the image (i.e., in sonography the structure of interest typically appears in the middle of the image). Therefore, for example, if an image contains two anatomical structures, the Euclidean distance feature, d, can learn to classify the image according to the structure that appears closer to center of the image. The number of features in this feature set can be small (e.g., if we have 77 templates then the size of this feature vector is 77×3=231) but highly discriminative between some structures (e.g., head TV vs spine).

Figure 7A:
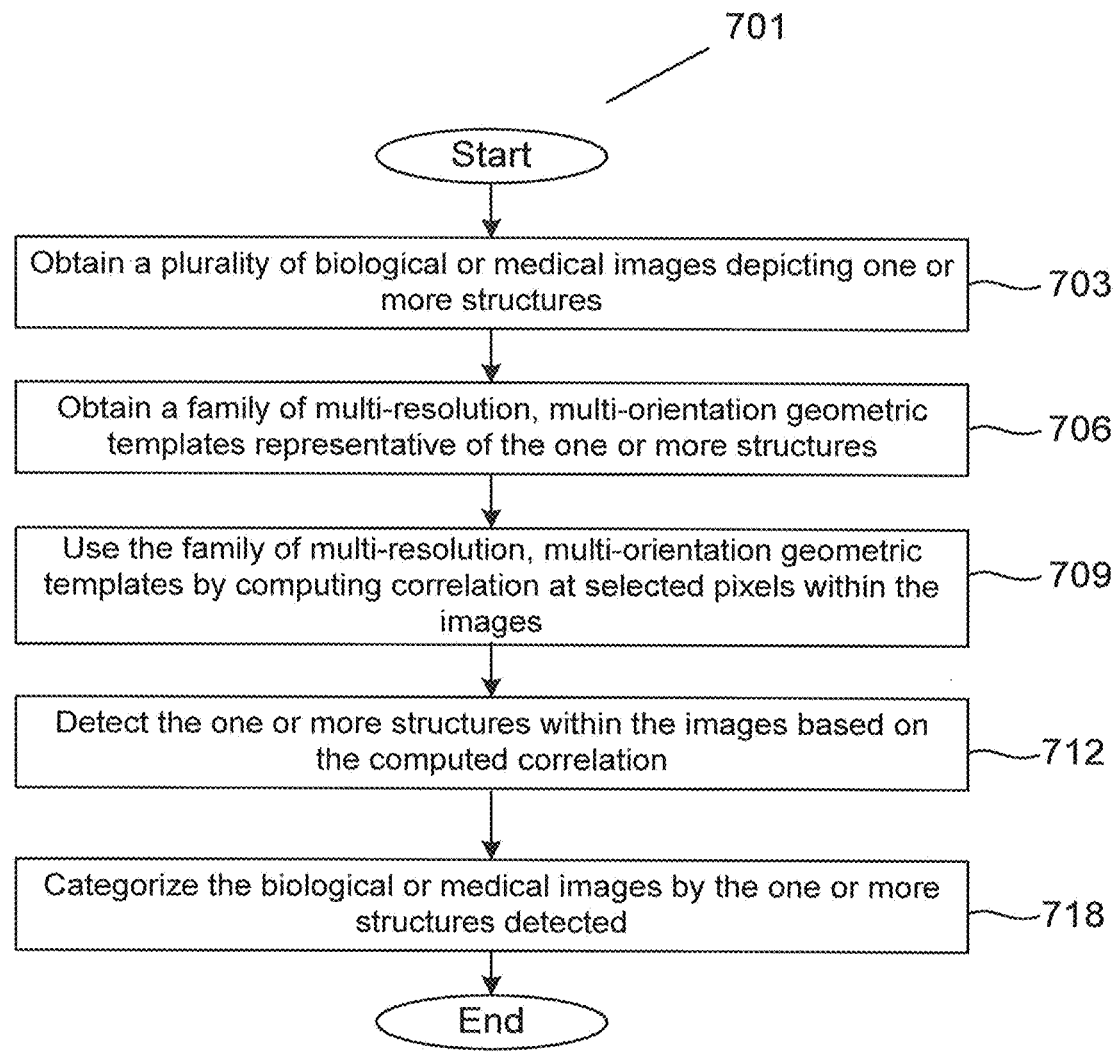
FIGS. 7A and 7B are various flow charts illustrating examples of functionality implemented as portions of a (A) structures detection and image categorization application and (B) appearance or intensity determination within a region of an image executed in the computing apparatus of FIG. 4 according to various embodiments of the present disclosure.

Thus, a system and method are provided for detecting and categorizing biological and medical images. The system and method can more quickly, efficiently and accurately process and categorize medical image(s). FIG. 7A is a flowchart generally depicting the method. The method starts 701 by obtaining 703 a plurality of biological or medical images depicting one or more structures. A family of geometric templates representative of the one or more structures can be obtained 706 or created. The family of geometric templates can be a family of multi-resolution, multi-orientation, invariant geometric templates as discussed herein. The family of geometric templates can be used 709 by computing a correlation of the template(s) to the images at selected pixels within the images. The computing correlation can be carried out as above. The correlation can be at each pixel within a selected region of interest or instead may be at every $n^{th}$ pixel within the image, where n is any number less than would be required to select each pixel. One or more structures within the images can be detected 712 based on the computed correlation. The clinical or biological images can then be categorized 718 based on the detection of the one or more structures based on the computed correlation.

However, the feature set may not be rich enough alone for good discrimination. For instance, the skull template may not distinguish between head TV and head TC, and the femur and spine templates can look similar and can provide similar responses.

In one or more aspects another feature set can be used, for example when the aforementioned feature set does not provide sufficient discrimination. For example, it can capture the appearance or intensity of a region (or ROI) within the image R. The appearance of the ROI can be captured by sectioning or splitting the region. In a non-limiting example, we can split the region, for example by splitting the region into a number of rows r and columns c which are selected by the learning algorithm. Splitting the region can allow multi-resolution distinction between regions (scaling invariance). In other words, if r and c are small, global appearance of the region is captured, while if r and c are as large as the number of rows and columns in the region then fine detail appearance can be learned.

Figure 3A:
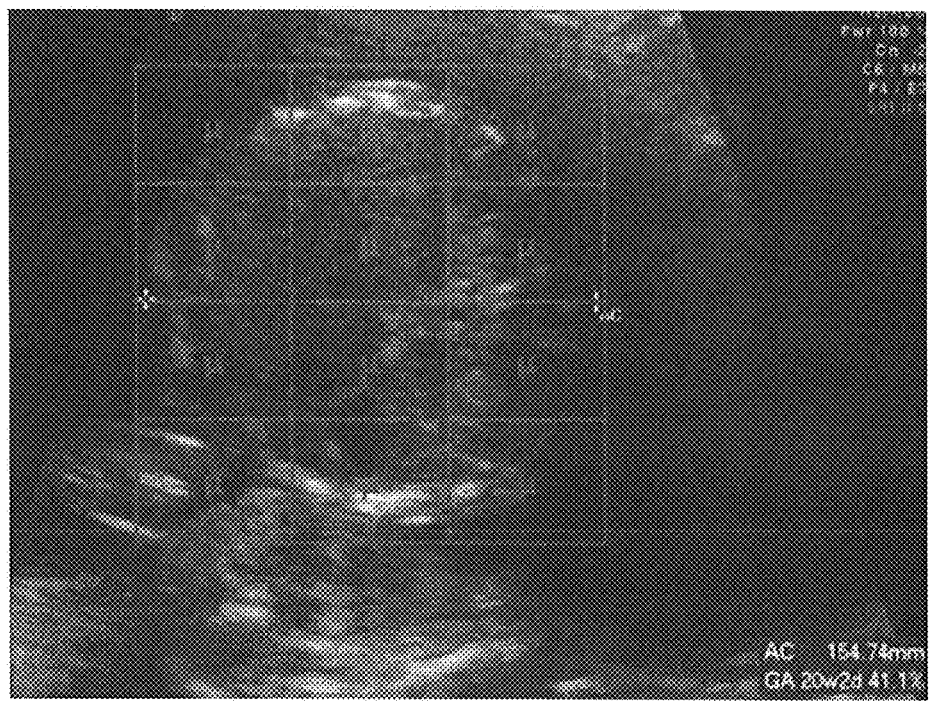
FIGS. 3A and 3B depict (A) an example region of 4×3 blocks on a fetal abdominal image, and (B) a feature matrix A.

FIG. 3A shows a candidate region split into 12 blocks. In general, the mean intensity can be computed inside each block k: [1, (r×c)]. To compute the relative appearance or intensity between blocks within a region, a square feature matrix A (as in FIG. 3B) of (r×c) rows and (r×c) columns can be computed as follows:

$$\bigvee \begin{bmatrix} i = 1:(r \times c) \\ j = 1:(r \times c) \end{bmatrix}, \quad (1)$$

$$A_{k_i,k_j} = \begin{cases} \text{Mean}(\text{block}_{k_i}) & |i = j \\ \text{Mean}(\text{block}_{k_i}) - \text{Mean}(\text{block}_{k_j}) & |i \neq j \end{cases},$$

A feature value can then be computed as $$f = \log_e(\det(A)): \text{det is the determination of a matrix} \quad (2)$$

Figure 3B:
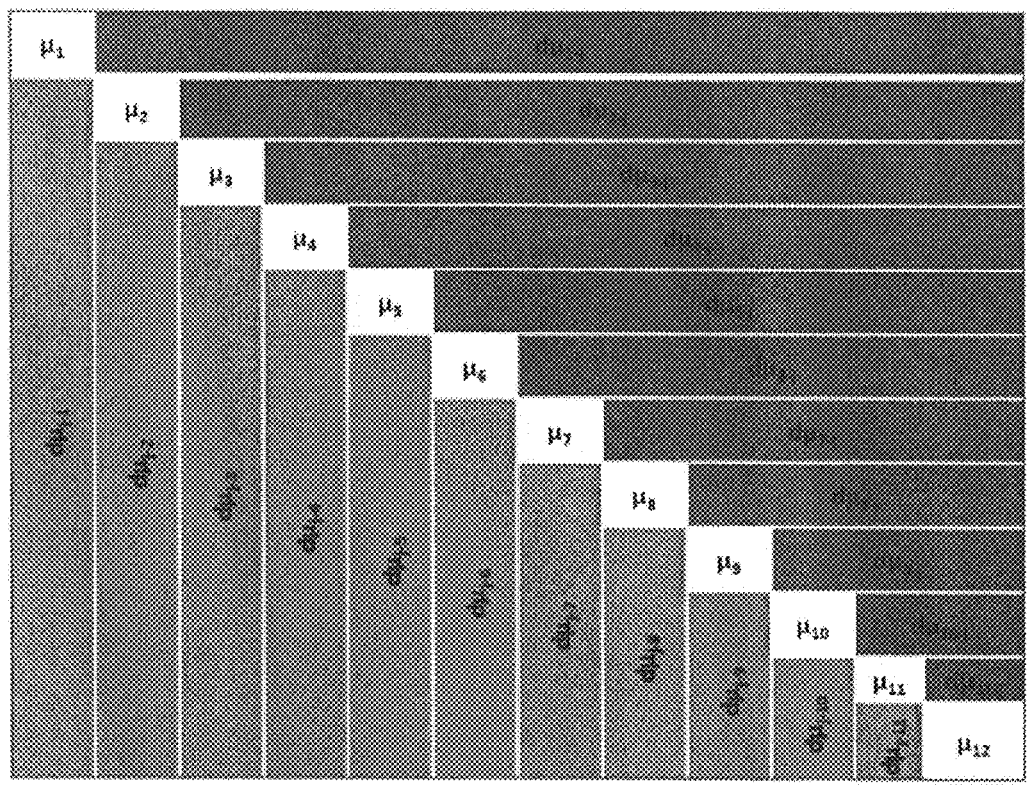
Figure 3C:
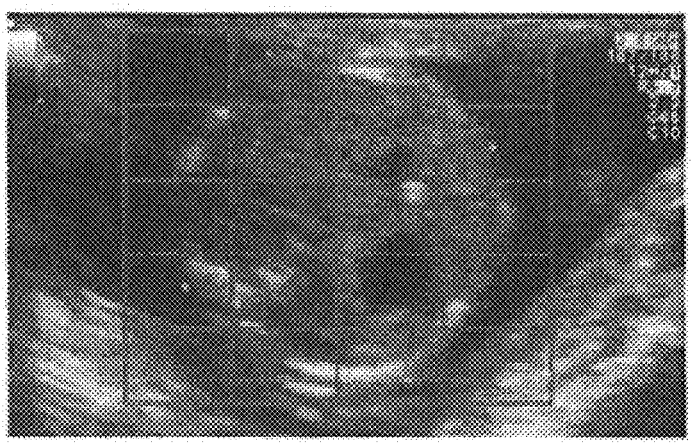
FIG. 3C depicts varying the partition size of the blocks to produce additional feature matrices A for the varying partitions.
Figure 3C:
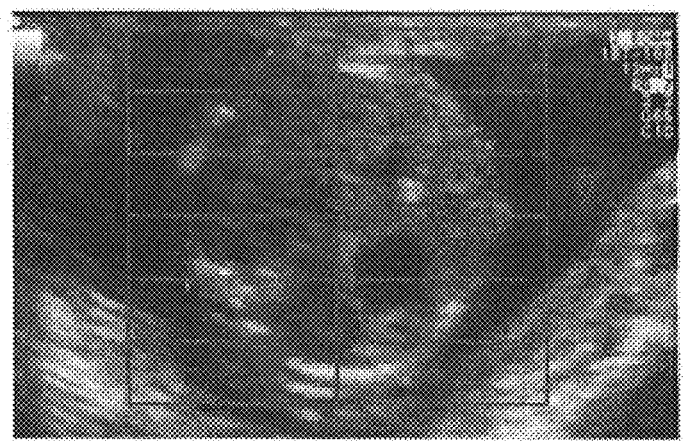
Figure 3C:
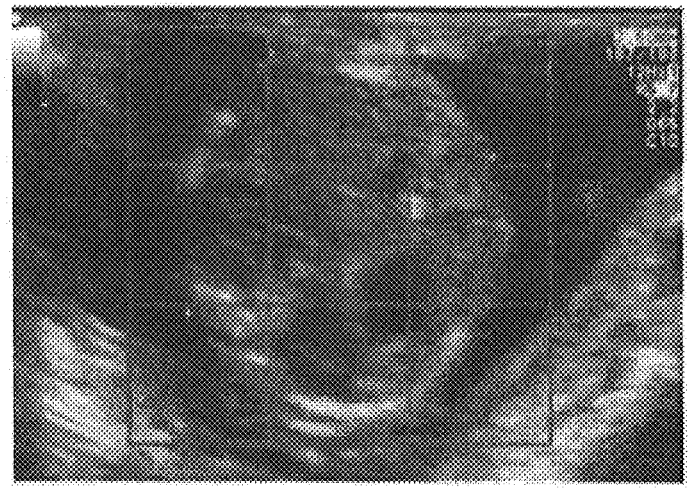
Figure 7B:
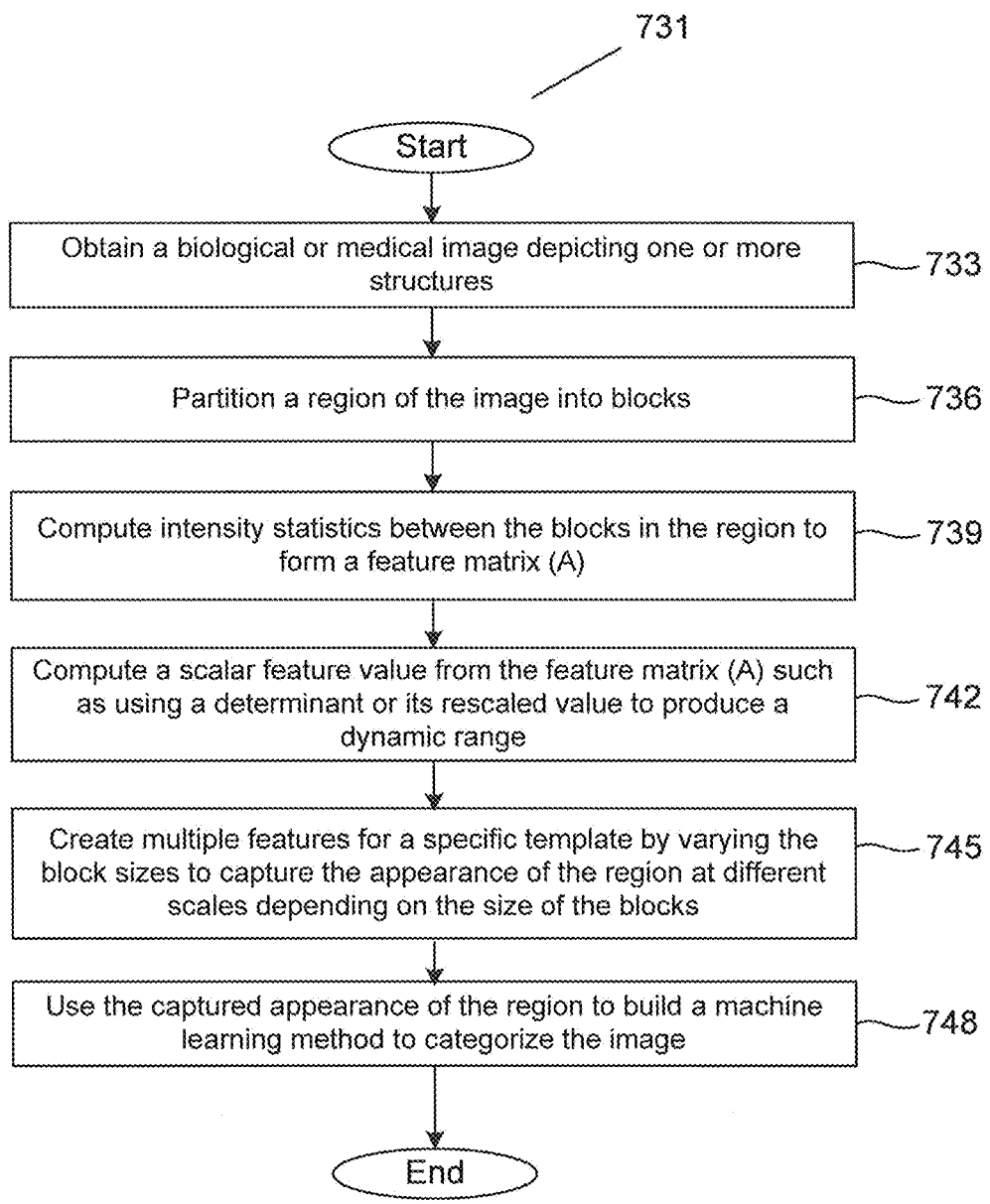

Thus, a system and method are provided for creating the feature matrix A as depicted in FIG. 3B and using Equations 1 & 2. FIG. 7B is a flowchart generally depicting the method. The method can start 731 by obtaining 733 a biological or medical image depicting one or more structures. A region of an image can be partitioned 736 into blocks. For example, the region of size R×C can be partitioned into blocks of size r×c (FIG. 3A). Intensity statistics can be computed 739 (e.g., mean, median, maximum, standard deviation, etc) between the blocks to form a feature matrix A as in FIG. 3B, e.g., using Equation 1. A scalar feature value can be computed 742 from the feature matrix such as using the determinant (A) or its rescaled value (e.g., using $\log_e$) to produce a convenient dynamic range, e.g., using Equation 2. Multiple features can be created 745 for a specific template by varying the block sizes r and c (as shown, for example in FIG. 3C). These features will capture the appearance of a region at different scales depending on the size of block i.e., the value of r & c. The captured appearance of the region can be used 748 to build a machine learning method or technique to categorize or label the image.

Because the location of a region is not fixed within the image, the computed feature over a region can be translation invariant. In addition, because the feature matrix A represents the variance between a given block and the rest of the blocks irrespective of block position within a region, this feature type can learn region appearance at different orientations.

The features computed as in the feature matrices A can be used to guide the learning algorithm. Given that we can compute template correlation scores, we can use these scores to weight the selection of features if needed to only use discriminative features from representative templates.

Training and Testing

Before training and testing, all images can be resized to the same pixel spacing to simplify correspondence between appearance features. A classifier was developed which can learn a fetal image category from a set of fetal ultrasound anomaly images. In a particular test a Random Forests (RF) classifier was used, though other classifiers can be used.

Training is performed on a set of images $\mathcal{I} = \{I_1, \ldots I_N\}$ such that N is the total number of images and their class labels $\mathcal{L} = \{L_1, \ldots L_N\}$ such that the $i^{th}$ training example is parameterized by $\{I_i, \{f_1, f_2, \ldots f_F\}, L_i\}$ where f is a feature from the feature pool of size F. The classifier can learn the best combination of the features (such as described in the Feature Sets section above) to build a set of trees. Each tree node can be created out of the best feature/threshold from a set of randomly sampled features from the feature pool. Once the best feature and threshold are found for a tree node, the list of training examples branch left and right and the training can proceed recursively on each subtree. A leaf node can be created if the maximum' tree depth is reached or if the number of training examples of a node is small. The set of training images reaching a leaf can be used to create a distribution which can be used to classify unseen images during testing.

Figure 4:
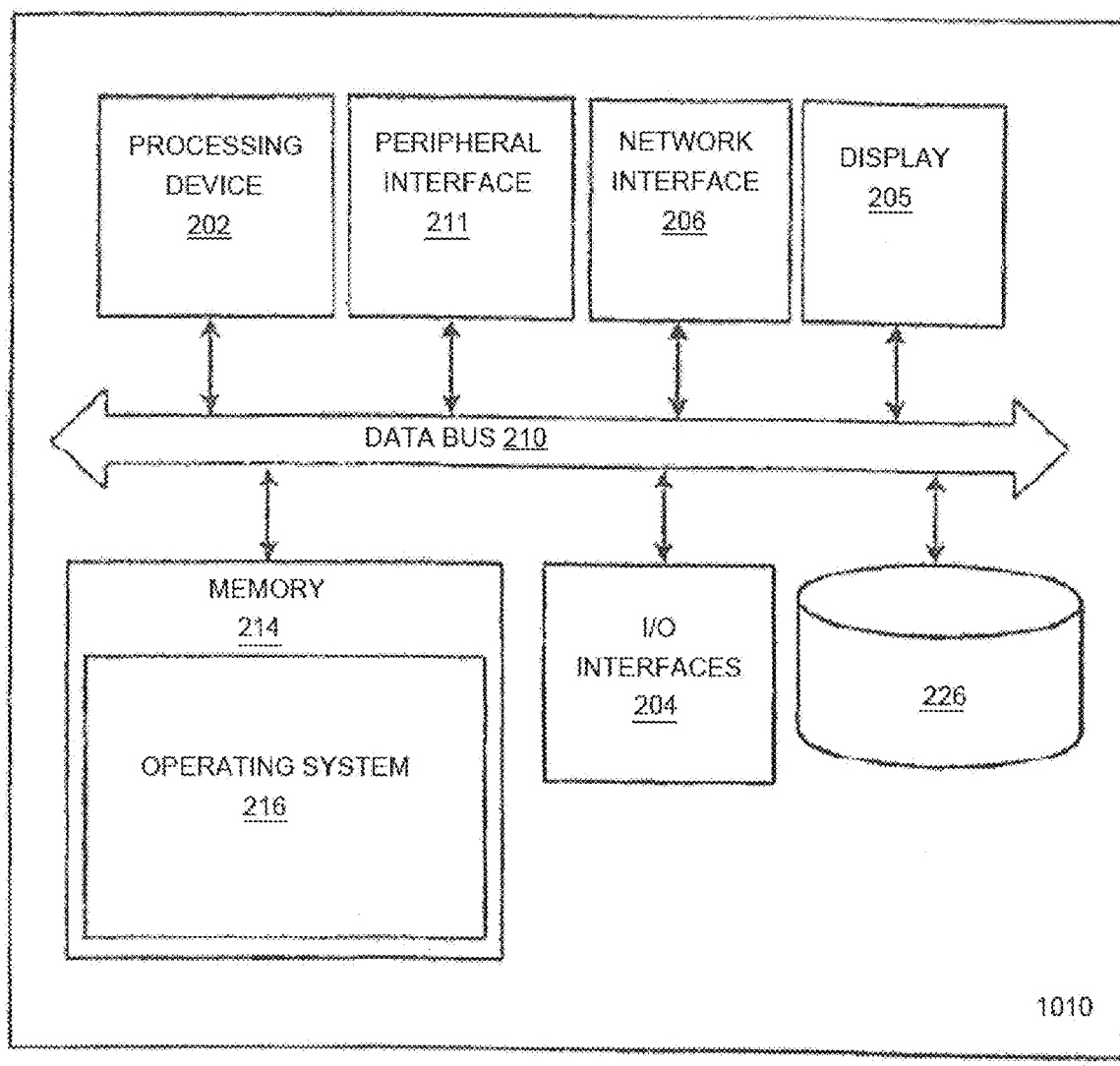
FIG. 4 is a schematic block diagram of an apparatus in which embodiments of the present systems and methods disclosed herein may be implemented.

Reference is now made to FIG. 4, which depicts an apparatus 1010 in which the present systems and methods described herein may be implemented, among others. The apparatus may include, for example, a medical imaging device, such as a sonogram or ultrasound device or a magnetic resonance imaging (MRI) device, or other device, by which medical images can be acquired. As can be understood, however, the apparatus may not include a medical imaging device as the one or more medical images may be acquired separately for example off-line, and simply provided to the apparatus for categorization. The apparatus 1010 may be embodied in any one of a wide variety of wired and/or wireless computing devices, multiprocessor computing device, and so forth.

As shown in FIG. 4, the apparatus 1010 comprises memory 214, a processing device 202, one or more input/output interfaces 204, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211. The apparatus may be a stand-alone apparatus, or may be incorporated into a network in which case a network interface 206 can be included.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system. In various aspects herein, the processing device more quickly, efficiently and accurately processes and categorizes one or more medical images as a result of implementation of the present methods.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for structures detection and image categorization described herein. In accordance with such embodiments, the application specific software can be stored in memory 214 and executed by the processing device 202. One of ordinary skill in the art will appreciate that the memory 214 can, and typically will, comprise other components which have been omitted for purposes of brevity.

The one or more input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, a touch screen or other display device.

In an embodiment of this disclosure, a non-transitory computer-readable medium stores one or more programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical)

With further reference to FIG. 4, network interface device 206 comprises various components used to transmit and/or receive data over a network environment. The components can be used, for example, to transmit and/or receive the medical images to be categorized and/or the one or more templates described herein. For example, the network interface 206 may include a device that can communicate with both inputs and outputs, for instance, a modulator/demodulator (e.g., a modem), wireless (e.g., radio frequency) transceiver, a telephonic interface, a bridge, a router, network card, etc.). The apparatus 1010 may communicate with one or more computing devices (not shown) via the network interface 206 over the network 118 (not shown). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 4 may be embodied, for example, as a medical imaging device, which includes a processing module or logic for performing conditional data processing, and may be implemented either off-line or directly in a medical imaging device. For such embodiments, the apparatus 1010 may be implemented as a device with medical image processing capabilities, and direct implementation makes it possible to acquire the medical images to be categorized and made available for viewing.

The methods of FIGS. 7A and 7B show examples of functionality that can be implemented in the apparatus 1010 of FIG. 4. If embodied in software, each step shown in FIGS. 7A and 7B may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 4) in a computer system or other system. The machine code may be converted from the source code, etc. If embodied in hardware, each block may represent a circuit or a number of interconnected circuits to implement the specified logical function(s).

Although FIGS. 7A and 7B show a specific order of execution, it is understood that the order of execution may differ from that which is depicted. For example, the order of execution of two or more steps may be scrambled relative to the order shown. Also, two or more steps shown in succession in FIGS. 7A and 7B may be executed concurrently or with partial concurrence. Further, in some embodiments, one or more of the steps shown in FIGS. 7A and 7B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

Experiments

To test the present system and method a number of experiments were carried out, described below.

Dataset

We first obtained a data set of images to be categorized. 29858 2D fetal ultrasound images from 2256 routine anomaly scans undertaken in the 12 months of 2013 between 18 weeks+0 days to 22 weeks+6 days were used from a hospital database. These scans were acquired by 22 different sonographers so there is large (but typical) variation in image quality, machine settings, and zoom aspects. No attempt was made to reject or remove any scans from the dataset as we intended to evaluate our method on a real-world dataset. The reported results thus show potential performance in real world deployment.

The dataset contained fetal head (TV and TC), abdomen, femur, spine, face, cardio, and several other categories as specified in the standard screening protocol in the hospital. Scans were acquired on GE Voluson E8 machines (GE Healthcare, Milwaukee USA). All images were anonymized before analysis, and their use underwent institutional board approval.

Evaluation Protocol & Metrics

The accuracy of the template matching was visually assessed. The effect of the features was investigated by comparing the guided Random Forests (RF) classifier with a traditional RF classifier using standard generalized Haar wavelets used in many medical image applications including object segmentation and detection in MRI, CT and ultrasound images [11-16]. These features compute the difference of mean intensity of two random blocks. The whole image was considered when sampling features and the center of the image was used as a reference point for those features. In addition, the categories that were found confusing were investigated to gain further understanding of the algorithm performance. The particular categories investigated were: head TV, head CV, cardio, abdomen, spine, femur, face, others and overall.

We performed 10-fold cross-validation, and we selected Random Forests (RF) parameters experimentally. The RF parameters selected were the maximum tree depth and the number of tress. These were then fixed in all reported experiments. Maximum tree depths of 18 and 30 trees were used. RF produces probabilities during testing. An image is correctly classified (defined by the true positives TP), if its class has the maximum probability among all other class probabilities. We report the accuracy of a method as (acc=TP/N). However, due to the complexity of fetal images and the occurrence of multiple structures in many images, we also report $acc_{top2}=TP_{top2}/N$ (as used in many machine learning imaging papers e.g., [17, 18]). An image is considered in $TP_{top2}$ if its class is within the top 2 probabilities produced by the trained RF. Finally, all experiments were implemented in Matlab and all RF methods were trained and tested in a parallel manner to achieve fast implementation. Given an unseen image, the Guided RF method categorizes it in approximately 0.32 of a second on a high end workstation with 20 processing units.

Results

FIGS. 2A-2C show visual results of localization of objects of interest where boxes are drawn around the matched regions for the different templates. Only the best-matched templates are shown. Each color represents a different template type as described in the Localizing Objects of Interest section above. The width of the box border signifies the strength of the template response. The over-all accuracy of the traditional RF to correctly classify the images to one of the eight categories was 65% while the Guided RF method achieved 75% accuracy.

Figure 5A:
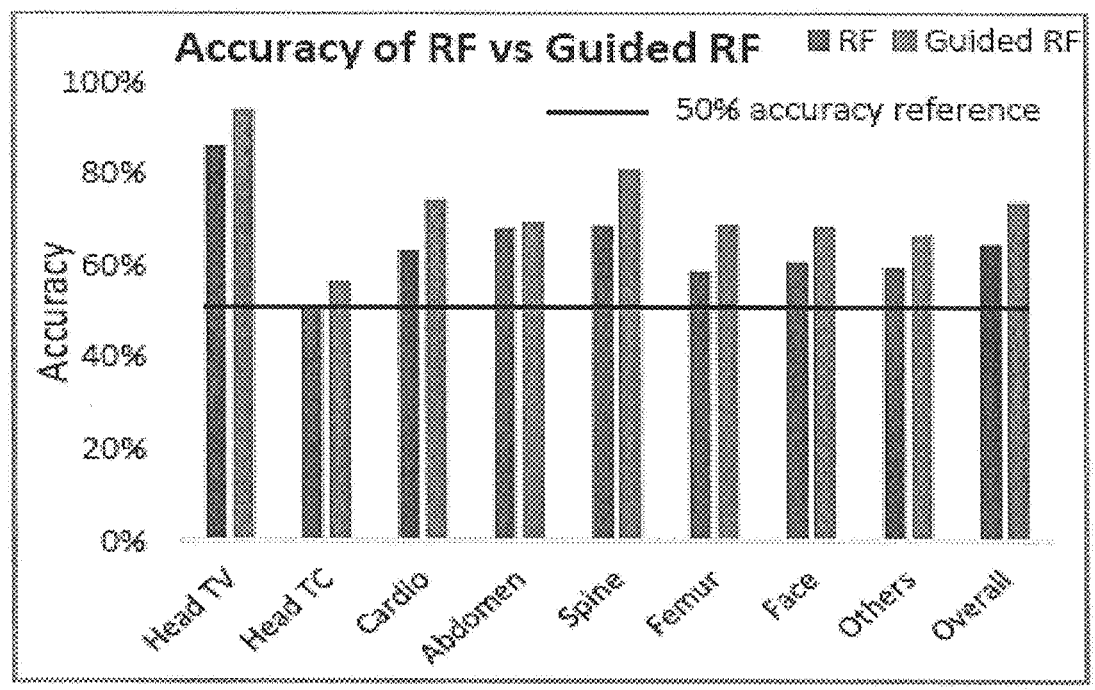
FIGS. 5A and 5B depict a comparison of accuracy of our present method on different image categories, proving accuracy of both: (A) accuracy of the machine learning based approach decision based on the top probability; and (B) accuracy of the machine learning approach based on the top 2 probabilities.
Figure 5B:
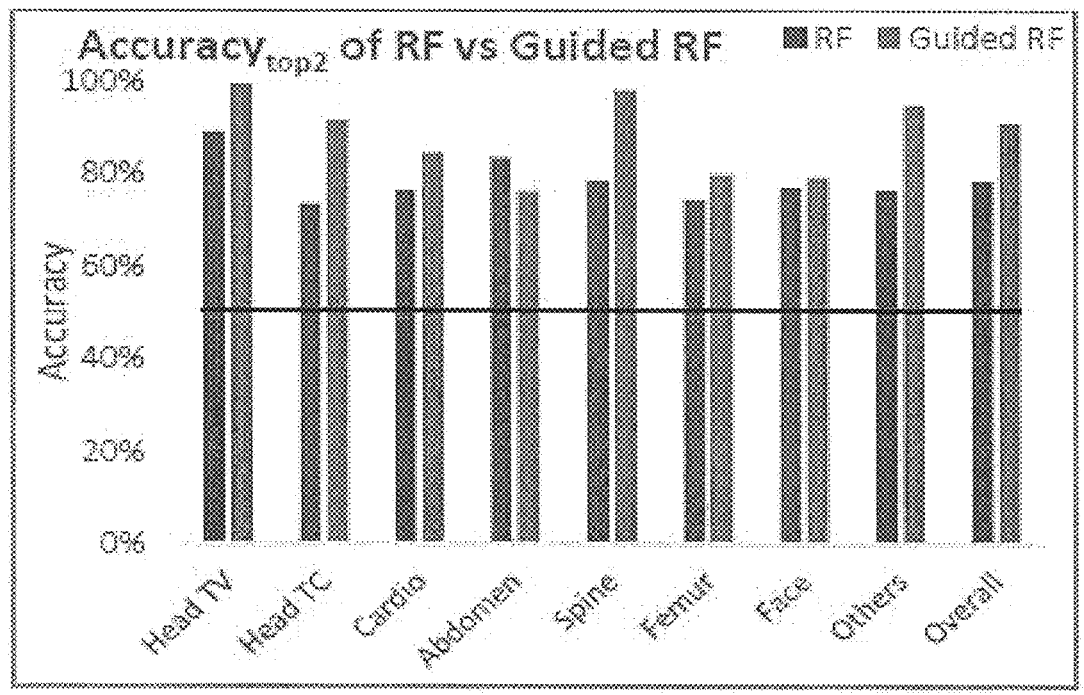
Figure 6:
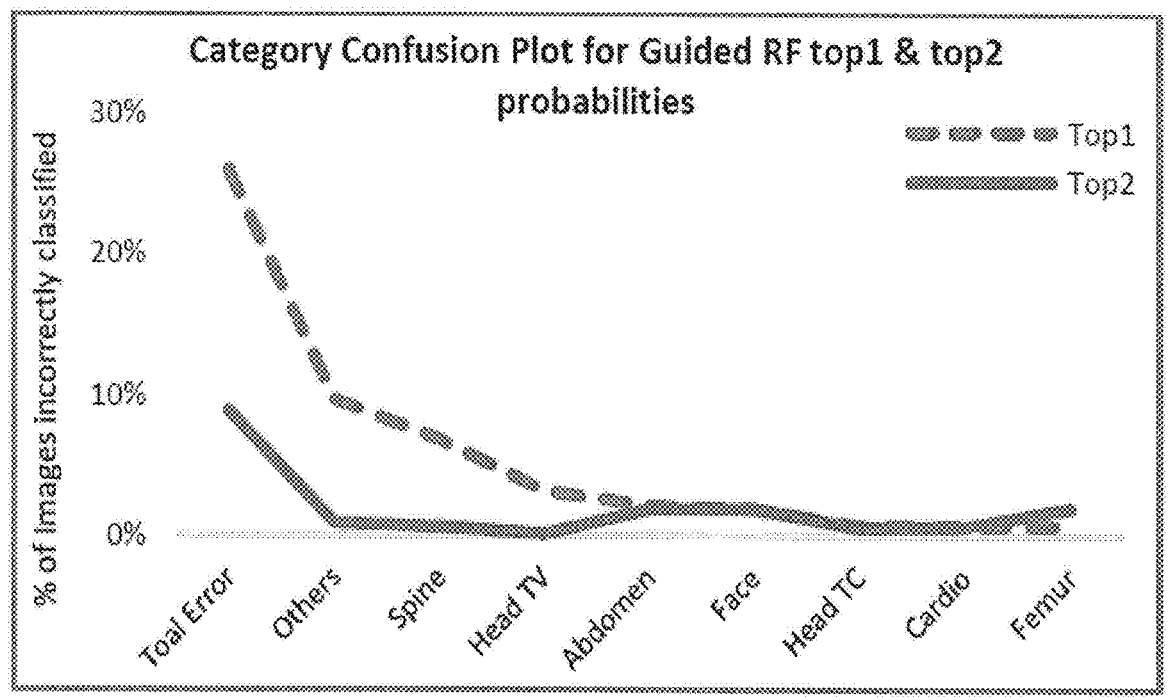
FIG. 6 depicts a Category Confusion Plot, showing misleading categories in descending order for the particular dataset.

A detailed comparison on the different classes is shown in FIG. 5A. FIG. 5B shows the accuracy$_{top2}$ result for both the traditional RF and the Guided RF method. Guided RF increased to 91% accuracy when considering the top 2 probabilities from RF output while the accuracy of the traditional RF increased to 79%. Finally, FIG. 6 shows the category confusion plot which presents the different categories in descending order with respect to how often images get classified in each category. Note that the most common error is for one of the eight classes to be misclassified as "Others" as opposed to being confused with another named fetal class.

CONCLUSIONS

Thus, presented herein are a new system and method for structures detection and categorization in biological and medical imaging. In an embodiment it can be a machine learning solution to categorize biological and medical images, such as fetal ultrasound images. The classifier can be guided to provide good classification via guided sampling of features from ROIs. In various aspects, a method is provided to detect ROIs within the images that can use template matching to allow the classifier to learn from these regions and ignore misleading regions and structures. Also provided is a new feature type which can capture a region within an image such that this feature is translation, orientation and/or scaling invariant. This type of feature can be important because, for example, the position and orientation of fetal structures may depend on the location of the fetus in the womb which is highly variable, see FIGS. 5A and 5B.

Because of the complexity of the "Others" group and the existence of many images in this group which look similar to the other 7 groups (e.g., cord insertion images are very similar to abdominal images), many images can get sorted as "Others". This can be seen in FIG. 6. Also, note that the "Spine" group may also be confusing as its appearance is similar to different structures, e.g., femur and diaphragm which is in the "Others" group. A multi-class solution which accommodates context of other labels can solve this problem. Finally, while we tested 2D ultrasound, our method is generalizable and can be extended to 3D medical imaging, including 3D ultrasound and other imaging modalities.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES

[1] R. F. Murray, "Classification images: A review," Journal of Vision, vol. 11, May 1, 2011.

[2] A. Bosch, X. Muñoz, and R. Marti, "Review: Which is the best way to organize/classify images by content?," Image Vision Computing, vol. 25, pp. 778-791, 2007.

[3] D. Lu and Q. Weng, "A survey of image classification methods and techniques for improving classification performance," Int. J. Remote Sens., vol. 28, pp. 823-870, 2007.

[4] G. Carneiro, B. Georgescu, S. Good, and D. Comaniciu, "Detection and Measurement of Fetal Anatomies from Ultrasound Images using a Constrained Probabilistic Boosting Tree," IEEE Transactions on Medical Imaging, vol. 27, pp. 1342-1355 2008.

[5] B. G. Prasad and K. A. N, "Classification of Medical Images Using Data Mining Techniques," in *Advances in Communication, Network, and Computing*. vol. 108, 2012, pp. 54-59.

[6] H. Greenspan and A. T. Pinhas, "Medical Image Categorization and Retrieval for PACS Using the GMM-KL Framework," *Information Technology in Biomedicine, IEEE Transactions on*, vol. 11, pp. 190-202, 2007.

[7] M. Maraci, R. Napolitano, A. Papageorghiou, and J. A. Noble, "Object Classification in an Ultrasound Video Using LP-SIFT Features," in *Medical Computer Vision: Algorithms for Big Data*, Springer International Publishing, 2014, pp. 71-81.

[8] D. Ni, X. Yang, X. Chen, C.-T. Chin, S. Chen, P. A. Heng, et al., "Standard Plane Localization in Ultrasound by Radial Component Model and Selective Search," *Ultrasound in Medicine & Biology*, vol. 40, pp. 2728-2742, 2014.

[9] M. Fernández-Delgado, E. Cernadas, S. Barro, and D. Amorim, "Do we Need Hundreds of Classifiers to Solve Real World Classification Problems?," *Journal of Machine Learning Research*, vol. 15, pp. 3133-3181, 2014.

[10] A. T. Papageorghiou, E. O. Ohuma, D. G. Altman, T. Todros, L. C. Ismail, A. Lambert, et al., "International standards for fetal growth based on serial ultrasound measurements: the Fetal Growth Longitudinal Study of the INTERGROWTH-21st Project," *The Lancet*, vol. 384, pp. 869-879, 2014.

[11] K. Chykeyuk, M. Yaqub, and J. A. Noble, "Novel Context Rich LoCo and GloCo Features with Local and Global Shape Constraints for Segmentation of 3D Echocardiograms with Random Forests," in *Medical Computer Vision. Recognition Techniques and Applications in Medical Imaging*. vol. 7766, Springer Berlin Heidelberg, 2013, pp. 59-69.

[12] A. Criminisi, J. Shotton, D. Robinson, and E. Konukoglu, "Regression Forests for Efficient Anatomy Detection and Localization in CT Studies," in Medical Computer Vision: Recognition Techniques and Applications in Medical Imaging, 2010.

[13] E. Konukoglu, B. Glocker, D. Zikic, and A. Criminisi, "Neighbourhood Approximation Forests," in Medical Image Computing and Computer-Assisted Intervention, 2012.

[14] O. Pauly, B. Glocker, A. Criminisi, D. Mateus, A. M. Moller, S. Nekolla, et al., "Fast Multiple Organs Detection and Localization in Whole-Body MR Dixon Sequences," in Medical Image Computing and Computer Assisted Intervention, Toronto, Canada, 2011.

[15] M. Yaqub, M. K. Javaid, C. Cooper, and J. A. Noble, "Investigation of the Role of Feature Selection and Weighted Voting in Random Forests for 3-D Volumetric Segmentation," *IEEE Transactions on Medical Imaging*, vol. 33, pp. 258-271, 2014.

[16] M. Yaqub, A. Kopuri, S. Rueda, P. Sullivan, K. McCormick, and J. A. Noble, "A Constrained Regression Forests Solution to 3D Fetal Ultrasound Plane Localization for Longitudinal Analysis of Brain Growth and Maturation," in *Machine Learning in Medical Imaging. vol.* 8679, Springer International Publishing, 2014, pp. 109-116.

[17] K. Alex, I. Sutskever, and E. H. Geoffrey, "ImageNet Classification with Deep Convolutional Neural Networks," in *Advances in Neural Information Processing Systems,* 2012, pp. 1097-1105.

[18] O. Russakovsky, J. Deng, H. Su, J. Krause, S. Satheesh, S. Ma, et al., "ImageNet Large Scale Visual Recognition Challenge," *Computer Vision and Pattern Recognition,* vol. arXiv:1409.0575, 2014.

The invention claimed is:

1. A method for categorizing biological or medical images, comprising:
   a) obtaining a plurality of biological or medical images depicting one or more structures;
   b) providing and using a family of multi-resolution, multi-orientation geometric templates that is made translation, orientation and/or scaling invariant by computing correlation with the templates at selected pixels within the images;
   c) detecting the one or more structures within the images based on the computed correlation; and
   d) categorizing the biological or medical images by the one or more structures detected.

2. The method of claim 1, wherein the geometric templates are selected from the group consisting of geometric templates of manufactured parts, biological or medical anatomical applications.

3. The method of claim 2, wherein the step of computing correlation is carried out using a parameter selected from the group consisting of a template correlation value, a relative size of the region with respect to the original image size, a Euclidean distance measured between the center of the region $\underline{C}=\{cx, cy\}$ and a center of the image, a location of the top left corner of the region within the image, a location of the bottom right corner of the region, and combinations thereof.

4. The method of claim 1, wherein the step (c) of detecting the one or more structures includes discriminating between the image of the one or more structures and misleading structures in the biological or medical images.

5. The method of claim 1, wherein the family of geometric templates is based on clinical knowledge of known biology or anatomy.

6. The method of claim 1, wherein the step of computing correlation is carried out using a parameter selected from the group consisting of a template correlation value, a relative size of the region with respect to the original image size, a Euclidean distance measured between the center of the region $C=\{cx, cy\}$ and a center of the image, a location of the top left corner of the region within the image, a location of the bottom right corner of the region, and combinations thereof.

7. The method of claim 6, wherein the correlation is carried out in the spatial or the Fourier domain.

8. The method of claim 6, wherein the step of detecting the one or more structures within the images involves a machine learning technique to look for features in a representative region or regions within the images to be categorized.

9. The method of claim 8, wherein the machine learning technique is a Random Forests machine learning technique.

10. The method of claim 6, wherein the family of geometric templates is based on clinical knowledge of known biology or anatomy.

11. The method of claim 1, wherein the correlation is carried out in the spatial or the Fourier domain.

12. The method of claim 1, wherein the step of detecting the one or more structures within the images involves a machine learning technique to look for features in a representative region or regions within the images to be categorized.

13. The method of claim 12, wherein the machine learning technique is a Random Forests machine learning technique.

14. A system for categorizing clinical or biological images, comprising:
   at least one device for receiving a plurality of biological images depicting one or more structures and a family of multi-resolution, multi-orientation geometric templates that is made translation, orientation and/or scaling invariant by computing correlation at selected pixels within the images;
   at least one computing device; and
   an application executable in the at least one computing device, the application comprising logic that:
   a) uses the family of multi-resolution, multi-orientation geometric templates by computing correlation with the templates at the selected pixels within the images;
   b) detects the one or more structures within the images based on the computed correlation; and
   c) categorizes the biological or medical images by the one or more structures detected.

15. A non-transitory computer readable medium employing a program executable in at least one computing device, comprising code that:
   a) receives a plurality of the biological or medical images depicting one or more structures and a family of multi-resolution, multi-orientation geometric templates that is made translation, orientation and/or scaling invariant;
   b) uses the family of multi-resolution, multi-orientation geometric templates by computing correlation with the templates at the selected pixels within the images;
   c) detects the one or more structures within the images based on the computed correlation; and
   d) categorizes the biological or medical images by the one or more structures detected.

* * * * *